US006280762B1

(12) United States Patent
Bealin-Kelly et al.

(10) Patent No.: US 6,280,762 B1
(45) Date of Patent: Aug. 28, 2001

(54) CENTER FILLED CONFECTIONERY

(75) Inventors: Francis Joseph David Bealin-Kelly, Surrey (GB); Bernhard Hanke, Bad Schwalbach; Paul Nienaber, Ingelheim, both of (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/403,377

(22) PCT Filed: Apr. 14, 1998

(86) PCT No.: PCT/IB98/00558

§ 371 Date: Oct. 20, 1999

§ 102(e) Date: Oct. 20, 1999

(87) PCT Pub. No.: WO98/47484

PCT Pub. Date: Oct. 29, 1998

(30) Foreign Application Priority Data

Apr. 21, 1997 (GB) ................................................ 9707977

(51) Int. Cl.⁷ ............................. A61K 9/68; A61K 47/00; A23G 3/00
(52) U.S. Cl. ........................ 424/440; 424/439; 424/464; 426/658; 426/660
(58) Field of Search ................................ 424/439, 440, 424/464; 426/658, 660

(56) References Cited

U.S. PATENT DOCUMENTS

| 3,894,154 | 7/1975 | Graff et al. ........................... 426/5 |
|---|---|---|
| 4,136,163 | 1/1979 | Watson et al. ........................ 424/54 |
| 4,157,402 | 6/1979 | Ogawa et al. ........................ 426/5 |
| 4,230,688 | 10/1980 | Rowsell et al. ..................... 424/45 |
| 4,250,196 | 2/1981 | Friello ................................... 426/5 |
| 4,372,942 | 2/1983 | Cimiluca .............................. 424/16 |
| 4,466,983 | 8/1984 | Cifrese et al. ........................ 426/5 |
| 4,517,205 | * 5/1985 | Aldrich ............................... 426/103 |
| 4,762,719 | 8/1988 | Forester .............................. 424/440 |
| 4,774,094 | * 9/1988 | Carroll et al. ......................... 426/3 |
| 5,002,791 | 3/1991 | Knebl ................................. 426/660 |
| 5,458,894 | 10/1995 | Knebl et al. ........................ 426/231 |
| 5,912,007 | * 6/1999 | Pan et al. ............................ 424/440 |

FOREIGN PATENT DOCUMENTS

| 0140085 | 9/1984 | (EP) . |
|---|---|---|
| 0431376 | 11/1990 | (EP) . |
| 0534823 | 9/1992 | (EP) . |
| 1452291 | 8/1973 | (GB) . |
| WO9702273 | 1/1997 | (WO) . |
| WO9706695 | 2/1997 | (WO) . |

\* cited by examiner

*Primary Examiner*—Thurman K. Page
*Assistant Examiner*—S. Tran
(74) *Attorney, Agent, or Firm*—L. M. White; J. M. Howell; K. F. Clark

(57) ABSTRACT

A throat drop comprises from 60 to 95% of a candy shell and from 5 to 40% of an aqueous filling, by weight of the drop. The filling comprises, by weight, by 8 to 20% water, from 50 to 85% bulk sweetener, and sufficient emulsifier to provide a contact angle of from 90° to 120°, the filling having a contact angle of greater than 120° in the absence of the emulsifier. The reduction in contact angle relative to a composition without the emulsifier provides an improved perception of liquidity of the filling.

26 Claims, No Drawings

CENTER FILLED CONFECTIONERY

FIELD OF THE INVENTION

The present invention relates to liquid centre-filled confectionery, especially liquid centre-filled throat drops, for soothing of irritated throats and nasal passages.

BACKGROUND OF THE INVENTION

Products in the form of cough drops have long been known as vehicles for the delivery of medicaments aimed at soothing sore or irritated throats. Such medicaments include analgesics, antitussives, expectorants, cooling agents such as menthol, and warming agents such as ethanol or gingerol. The medicament can be administered by way of a throat drop or lozenge which releases the active agent upon sucking. Particularly in the case of a volatile active agent, the product can also provide relief from cold symptoms by way of clearing the nasal passages.

EP-A-431,376, for example, describes hard confections for sustained release treatment of sore throats comprising hydrogenated isomaltulose and an active ingredient which can be an antitussive or antihistamine but can also be a volatile oil such as menthol or eucalyptus. The confection normally contains a further flavouring agent such as lemon, honey or cherry but which can also be menthol or eucalyptus.

A well accepted form of throat drop is a centre-filled throat drop consisting of an edible shell and a liquid centre-filling. The liquid centre provides a pleasant soothing effect on the throat which may be further enhanced by an active agent as described above.

One of the problems with such throat drops is to provide the optimum degree of liquidity in the centre filling. Typically the edible shell cannot tolerate a high degree of moisture in the filling for reasons of product stability. Levels of moisture in the filling are usually less than 20%. The bulk of the filling usually comprises a bulk sweetener to improve the palatability of the product. These constraints often mean that the viscosity of the filling is rather high, say in excess of 50,000 mPa.s, resulting in a reduction in perception of liquidity of the centre.

U.S. Pat. No. 3,894,154 discloses the inclusion of a glycerine in the centre of liquid centre-filled chewing gum for retarding increases in viscosity of the liquid fill portion. Whilst such an approach is effective, especially within a corn syrup base, it is often not of itself sufficient.

U.S. Pat. No. 4,157,402 discloses the use of an emulsifier in the filling of a centre-filled chewing gum to prevent the flavoured liquid filling penetrating into the surrounding gum composition, thus improving the flavour retaining capacity of the chewing gum.

It has now surprisingly been found that the addition of sufficient emulsifier to the liquid filling of a centre-filled hard candy to reduce its contact angle against a gelatine coated plate from more than 120° to a value in the range of 90 to 120°, is sufficient to provide an improvement in the perception of liquidity, and thus throat soothing, even though such addition may result in an increase in viscosity.

It is accordingly an object of this invention to provide centre-filled candy compositions, especially throat drops, with an improved perception of liquidity of the filling.

It is a further object of the invention to provide centre-filled throat drops, with an improved perception of throat soothing.

SUMMARY OF THE INVENTION

The present invention relates to a throat drop comprising from 60 to 95%, of a candy shell and from 5 to 40% of an aqueous filling, by weight of the drop, the filling comprising from 8 to 20% water, from 50% to 85% of a bulk sweetener and sufficient emulsifier to provide a contact angle of from 90 to 120°, the filling having a contact angle of greater than 120° in the absence of the emulsifier.

All levels and ratios are by weight, unless otherwise indicated. Percentages are by weight of the filling unless otherwise specified.

DETAILED DESCRIPTION OF THE INVENTION

The throat drops of the present invention comprise from 60 to 95%, preferably from 75 to 85%, of a candy shell and from 5 to 40%, preferably from 15 to 25%, of an aqueous filling, by weight of the drop.

Centre-filled hard candies are described in U.S. Pat. No. 4,372,942 and U.S. Pat. No. 4,466,983. A suitable sugar base for a hard candy shell comprises from about 30% to about 85% glucose syrup and from about 15% to about 70% sucrose. Alternatively, a sugar-free base can be used for the shell. Suitable sugar-free bases include bulk sweeteners such as isomalt, maltitol and sorbitol. Isomalt and maltitol are preferred. The inner surface of the shell can also have a separate edible lining to prevent or reduce interaction of the filling with the shell. The edible shell can also further comprise flavours and throat relief agents as described further below.

The aqueous filling comprises water at a level of from about 8 to about 20%, more preferably from about 10 to about 15% by weight of the filling. Levels of water higher than about 20% are unsuitable for the production of centre-filled hard candies.

The filling further comprises a bulk sweetener, such as a sugar, suitably at a level of from about 50 to 85%, preferably from about 60 to about 75% on a dry solids basis by weight of the filling. In one embodiment the filling comprises, by weight, from 5% to 80%, preferably from 50% to 75%, sugar. A preferred source of the sweetener is high fructose corn syrup which, being commercially available as an 85% active material of which the balance is essentially water, can also provide some, or even all, of the water required. Sugar free compositions comprising a sugar alcohol such as sorbitol can also be used.

An essential component of the filling is an emulsifier, present in sufficient quantity to provide a contact angle of from 90 to 120°, the filling having a contact angle of greater than 120° in the absence of the emulsifier. Preferably the filling comprises sufficient emulsifier to provide a contact angle of from 95 to 115°, preferably from 100 to 110°. The 'contact angle', as used herein is the static contact angle of a drop of the filling on a gelatine coated cover slip, measured using a surface tensiometer and optical measuring apparatus (such as those manufactured by Kruss, Germany). The gelatine coated cover slip, prepared by dip coating a glass cover slip in a hot gelatine solution and cooling, is used as a model for the human mucous membrane.

The emulsifier should be a food-grade material. Suitable emulsifiers include mono-and di fatty acid glycerides such as those based on soya oil e.g. Imwitor 440 from Huels, acetoglycerides such as Dynacet 211, monoglycerides esterified with citric acid, such as Imwitor 370, and lecithins such as the Topicithin range from Lucas Meyer, Germany. Preferred is soybean lecithin. Suitable levels of the emulsifier are from 0.001 to about 1%, more preferably from about 0.005 to about 0.1% and especially from about 0.01 to about 0.05% by weight of the filling.

An optional but desirable component of the throat drops of the present invention is a throat relief agent. By "throat relief agent" herein is meant any organic compound or mixture of compounds capable of providing relief to a person with a sore or irritated throat or nasal passage. Classes of throat relief agents include, but are not limited to analgesics, antitussives, expectorants, physiological cooling agents, physiological warming agents and mixture thereof. Preferably the throat relief agent is selected from physiological cooling agents, physiological warming agents and mixtures thereof. Suitable levels of the throat relief agent are from about 0.001 to about 10%, preferably from about 0.01 to about 5%, more preferably from about 0.1 to about 3% by weight of the aqueous composition.

Suitable physiological cooling agents are described in WO 97/06695, incorporated by reference herein. Preferred for use herein are physiological cooling agents selected from the group consisting of menthol, peppermint oil, N-substituted-p-menthane-3-carboxamides, acyclic tertiary and secondary carboxamides, 3-1-menthoxy propan-1,2-diol and mixtures thereof. Particularly preferred for use herein are menthol and menthol containing oils such as peppermint oil.

The carboxamides found most useful are those described in U.S. Pat. No. 4,136,163, Jan. 23, 1979 to Watson et al., and U.S. Pat. No. 4,230,688, Oct. 28, 1980 to Rowsell et al. The carboxamides in U.S. Pat. No. 4,136,163 are N-substituted-p-menthane-3-carboxamides. N-ethyl-p-menthane-3-carboxamide, commercially available as WS-3 from Wilkinson Sword, is preferred herein. The carboxamides of U.S. Pat. No. 4,230,688 are certain acyclic tertiary and secondary carboxamides, of which trimethyl isopropyl butanamide, commercially available as WS-23 from Wilkinson Sword is preferred for use herein.

Preferred physiological warming agents are those selected from the group consisting of vanillyl alcohol n-butyl ether, vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, iso-amylalcohol, benzyl alcohol, chloroform, eugenol, cinnamon oil, cinnamic aldehyde, and phosphate derivatives thereof. The phosphate derivatives are those described in WO 97/02273, incorporated by reference herein.

The throat drops of the present invention can also comprise from 0.001 to 10% by weight of the filling of a vesicle-forming agent which acts to form vesicles which are dispersed within the filling and encapsulate the throat relief agent. By 'vesicle' is meant an essentially spherical structure comprising a lipid bilayer encapsulating a central core. The vesicles herein can be uni- or multi-lamellar and have a number average particle size of from about 1 to about 100 $\mu$m, more preferably from about 5 to about 50 $\mu$m. The particle size can be measured using an optical microscope, such as a Nikon Optiphoto 2, linked to an electronic image analysis system such as the Linkam MS100. Measurement can also be made using a graduated graticule in the field of view. EP-A-534,823, which describes anhydrous make-up compositions which can form vesicles on exposure to water gives a comprehensive list of amphiphilic liquids which can be used to form vesicles. Appropriately the emulsifier used herein is a vesicle forming agent. The preferred vesicle forming agent of the present invention is a plant-derived lecithins and, especially, soybean lecithin. Soybean lecithin can act to form vesicles at very low levels. Preferably the vesicle forming agent is present at a level of from about 0.001 to about 1%, more preferably from about 0.005 to about 0.1% and especially from about 0.01 to about 0.05% by weight of the filling. With adequate mixing, in the presence of water and a throat relief agent as described herein, the lecithin forms vesicles which encapsulate the throat relief agent.

It has further been found that the vesicle formation is enhanced by the presence of glycerine, which is preferably present at a level of from about 5 to about 25%, preferably from about 10 to about 20%, more preferably from about 12 to about 18% by weight of the filling. When the filling is a sugar-free base comprising a sugar alcohol, it is preferred that the sugar alcohol is employed in admixture with glycerine, since it has been found that sugar alcohols on their own can suppress vesicle formation.

The aqueous fillings herein can also include a flavouring agent. As used herein, the term 'flavouring agent' means those flavour essences and equivalent synthetic ingredients which are added to the flavour composition for the principal purpose of providing flavour to the confectionery product. It excludes throat relief agents as described above. Flavouring agents well known in the confectionery art can be added to the flavour compositions of the invention. These flavouring agents can be chosen from synthetic flavouring liquid and/or oils derived from plants leaves, flowers, fruits and so forth, and combinations thereof. Representative flavouring liquids include: artificial, natural or synthetic fruit flavours such as lemon, orange, banana, grape, lime, apricot and grapefruit oils and fruit essences including apple, strawberry, cherry, orange, pineapple and so forth; bean and nut derived flavours such as coffee, cocoa, cola, peanut, almond and so forth; and root derive flavours such as licorice. The amount of flavouring agent employed is normally a matter of preference subject to such factors as flavour type, base type and strength desired. In general, amounts up to about 4% by weight are usable with amounts of from about 0.1% to about 1% being preferred.

The aqueous filling can be made by straightforward mixing techniques. The general techniques for manufacturing centre-filled confectionery products can be found in the "Silesia Confiserie Manual No. 3", published by Silesia-Essenzenfabrik Gerhard Hanke K. G., Abt. Fachbücherei.

Suitably, fillings herein have a viscosity in the range of from about 5,000 to about 500,000, preferably from about 20,000 to about 250,000, more preferably from about 50,000 to about 100,000 mPa.s. The viscosity is measured at 25° C. at a shear rate of $50s^{-1}$ using a Physica Rheolab MC100 rheometer.

Centre-filled throat drops according to the invention can be manufactured by deposit, rope-forming and extrusion processes as known in the art. Extrusion and rope-forming processes are preferred. An example of an extrusion process is described in U.S. Pat. No. 5,458,894. An example of an extrusion process is described in U.S. Pat. No. 5,002,791.

The following examples are given to illustrate the compositions and uses according to the invention. However, the invention is not limited thereto.

EXAMPLE 1

Liquid, centre-filled throat drops were prepared according to formulae A and B below. The liquid filling was made by adding a premix of the lecithin, colour solution, flavour oils and/or cooling and warming agents to a mixture of the high fructose corn syrup pre-warmed to 82° C. The components were mixed for two minutes and co-extruded with a separately made candy base to produce centre-filled throat drops.

| | A Wt. % | B Wt. % |
|---|---|---|
| Candy casing (80% by wt. of drop) | | |
| Sucrose | 58.12 | 49.37 |
| Glucose syrup (80% solids) | 41.51 | 49.37 |
| Peppermint oil | 0.17 | — |
| Menthol | 0.17 | 0.08 |
| Lemon oil | — | 0.27 |
| Citric acid | — | 0.91 |
| | 100% | 100% |
| Liquid filling (20% by wt. of drop) | | |
| High fructose corn syrup[1] | 84.38 | 84.306 |
| Glycerine | 15.0 | 15.0 |
| Lecithin | 0.02 | 0.02 |
| Lemon oil | — | 0.314 |
| Colour (5% aqueous) | 0.32 | 0.16 |
| Peppermint oil | 0.15 | — |
| David Michael Heat[2] | 0.125 | 0.20 |
| Vanillin | 0.005 | — |
| | 100% | 100% |

[1]85% sugar solids, the balance being essentially water
[2]A warming agent available from David Michael & Co., Inc., Philadelphia, USA The liquid centre fillings have a contact angle of around 109° but a contact angle of about 126° in the absence of the lecithin. The throat drops deliver a pleasant throat soothing effect and provide an improved perception of liquidity of the filling.

What is claimed is:

1. A throat drop comprising from 60% to 95% of a candy shell and from 5% to 40% of an aqueous filling, by weight of the drop, the filling comprising, by weight of filling, from 8% to 20% water, from 50% to 85% of a bulk sweetener and sufficient emulsifier selected from the group consisting of mono-fatty acid glycerides, di-fatty acid glycerides, acetoglycerides, monoglycerides esterified with citric acid, lecithins and mixtures thereof to provide a contact angle of from 90 to 120°, the filling having a contact angle of greater than 120° in the absence of the emulsifier; wherein the filling has a viscosity in the range of from about 5,000 to about 500,000 mPa.s.

2. A throat drop according to claim 1, wherein the filling comprises sufficient emulsifier to provide a contact angle of from 95 to 115°.

3. A throat drop according to claim 1 wherein the emulsifier is soybean lecithin.

4. A throat drop according to claim 1 wherein the drop comprises from 75 to 85% of the shell and from 15 to 25% of the filling by weight of the drop.

5. A throat drop according to claim 1, wherein the filling comprises, by weight, from about 10% to about 15% water and from about 0.005% to about 0.1% emulsifier.

6. A throat drop according to claim 1, wherein the filling further comprises, by weight, from about 5% to about 25% glycerine.

7. A throat drop according to claim 1, wherein the filling comprises, by weight, from 5% to 80% sugar.

8. A throat drop according to claim 7 wherein the sugar is provided by high fructose corn syrup.

9. A throat drop according to claim 1 wherein the shell comprises a sugar-free base.

10. A throat drop according to claim 9 wherein the filling comprises a sugar alcohol.

11. A throat drop according to claim 10 wherein the sugar alcohol is in admixture with glycerine.

12. A throat drop according to claim 1 wherein the filling comprises a throat relief agent selected from the group consisting of physiological cooling agents, physiological warming agents and mixtures thereof.

13. A throat drop according to claim 1 wherein the filling has a viscosity in the range of from about 50,000 to about 100,000 mPa.s.

14. A throat drop according to claim 1, wherein the filling comprises from about 0.005% to about 0.1%, by weight, emulsifier.

15. A throat drop according to claim 14, wherein the filling comprises, by weight, from about 0.01% to about 0.05% emulsifier, and from about 10 to about 15% water.

16. A throat drop comprising:
   (a) a shell, and
   (b) an aqueous filling comprising water, sweetener and emulsifier selected from the group consisting of mono-fatty acid glycerides, di-fatty acid glycerides, acetoglycerides, monoglycerides esterified with citric acid, lecithins and mixtures thereof; wherein the filling has an improved perception of liquidity as compared to a filling which does not comprise the emulsifier.

17. A throat drop according to claim 16, wherein the filling comprises from about 0.005% to about 0.1%, by weight, emulsifier.

18. A throat drop according to claim 17, wherein the emulsifier is a lecithin, and the lecithin is present in the filling in the form of vesicles encapsulating a throat relief agent.

19. A throat drop according to claim 18, wherein the filling has a contact angle of from 90° to 120° and a viscosity in the range of from about 5,000 to about 500,000 mPa.s.

20. A throat drop according to claim 19, wherein the shell comprises an ingredient selected from the group consisting of flavours and throat relief agents.

21. A throat drop according to claim 20, wherein an inner surface of the shell has a separate edible lining.

22. A throat drop comprising:
   (a) a shell, and
   (b) an aqueous filling comprising, by weight of filling, from about 10% to about 15% water, from about 0.001% to about 10% throat relief agent and from about 0.001% to about 1% of an emulsifier selected from the group consisting of mono-fatty acid glycerides, di-fatty acid glycerides, acetoglycerides, monoglycerides esterified with citric acid, lecithins and mixtures thereof; wherein the filling has a viscosity in the range of from about 5,000 to about 500,000 mPa.s.

23. A throat drop according to claim 22, wherein the aqueous filling comprises, by weight, about 0.005% to about 0.1% emulsifier.

24. A throat drop according to claim 23, wherein the emulsifier is a lecithin, and the lecithin is present in the filling in the form of vesicles encapsulating the throat relief agent.

25. A throat drop according to claim 24, wherein the filling further comprises, by weight of the filling, from about 10% to about 20% glycerine.

26. A throat drop according to claim 25, wherein the confectionery filling has a contact angle of from 100° to 110° and a viscosity in the range of from about 50,000 to about 100,000 mPa.s.

* * * * *